United States Patent
Haribabu et al.

(10) Patent No.: US 12,263,083 B2
(45) Date of Patent: Apr. 1, 2025

(54) SYSTEMS FOR TRANSCATHETER PROSTHESIS DELIVERY AND METHODS

(71) Applicant: Medtronic, Inc., Minneapolis, MN (US)

(72) Inventors: Sumeeyae Haribabu, Ballybrit (IE); Malachy Magee, Banbridge (GB)

(73) Assignee: MEDTRONIC, INC., Minneapolis, MN (US)

( * ) Notice: Subject to any disclaimer, the term of this patent is extended or adjusted under 35 U.S.C. 154(b) by 292 days.

(21) Appl. No.: 17/675,153

(22) Filed: Feb. 18, 2022

(65) Prior Publication Data
US 2022/0354639 A1 Nov. 10, 2022

Related U.S. Application Data

(60) Provisional application No. 63/184,318, filed on May 5, 2021.

(51) Int. Cl.
*A61F 2/24* (2006.01)
*A61F 2/95* (2013.01)

(52) U.S. Cl.
CPC .......... *A61F 2/2418* (2013.01); *A61F 2/2433* (2013.01); *A61F 2/2466* (2013.01); *A61F 2/9517* (2020.05); *A61F 2210/00* (2013.01)

(58) Field of Classification Search
CPC ...... A61F 2/2427; A61F 2/243; A61F 2/2439; A61F 2/2418; A61F 2002/9511; A61F 2/9517; A61F 2230/0091; A61F 2/95; A61F 2/2433; A61F 2/2466; A61B 17/1214
See application file for complete search history.

(56) References Cited

U.S. PATENT DOCUMENTS

| | | | | |
|---|---|---|---|---|
| 5,709,702 A | * | 1/1998 | Cogita | ...................... A61F 2/88 606/198 |
| 5,851,232 A | * | 12/1998 | Lois | ...................... A61F 2/2412 623/1.13 |
| 7,803,185 B2 | | 9/2010 | Gabbay | |
| 9,364,324 B2 | | 6/2016 | Rafiee et al. | |
| 9,517,337 B2 | | 12/2016 | Ollivier | |
| 9,884,185 B2 | | 2/2018 | Ollivier | |
| 10,154,902 B2 | | 12/2018 | Rafiee et al. | |
| 10,376,364 B2 | | 8/2019 | Tamir et al. | |
| 10,575,950 B2 | | 3/2020 | McLean | |
| 2004/0117004 A1 | * | 6/2004 | Osborne | ................... C25F 3/24 623/1.36 |

(Continued)

*Primary Examiner* — Suzette J Gherbi
(74) *Attorney, Agent, or Firm* — Wentsler LLC

(57) ABSTRACT

Aspects of the disclosure include systems including a delivery device having a handle assembly, a shaft assembly having a distal portion, and a helical elongated member positioned at least partially over the shaft assembly and interconnected to the handle assembly. The system also includes a prosthesis positioned over the distal portion. The prosthesis has a stent frame having an inner surface and an outer surface, a valve structure positioned within the stent frame, and a track formed by one or more guides positioned on and extending from one of the inner or outer surfaces of the stent frame. The helical elongated member is configured to be moved in and out of the track to selectively compress or allow the prosthesis to expand. Methods of loading and delivering the prosthesis using systems of the disclosure are also disclosed.

20 Claims, 17 Drawing Sheets

(56) References Cited

U.S. PATENT DOCUMENTS

| | | |
|---|---|---|
| 2009/0318947 A1 | 12/2009 | Garcia et al. |
| 2011/0276121 A1 | 11/2011 | Levine |
| 2014/0214046 A1 | 7/2014 | Puckett |
| 2016/0184095 A1* | 6/2016 | Spence ................ A61F 2/2427 623/2.11 |
| 2017/0128205 A1 | 5/2017 | Tamir et al. |
| 2018/0040804 A1* | 2/2018 | Rasmussen ........ H10N 30/2027 |
| 2019/0060062 A1* | 2/2019 | Griffin ................ A61F 2/2439 |
| 2021/0169632 A1* | 6/2021 | Li ........................ A61F 2/2476 |

* cited by examiner

SYSTEMS FOR TRANSCATHETER PROSTHESIS DELIVERY AND METHODS

CROSS-REFERENCE TO RELATED APPLICATIONS

This Non-Provisional Patent Application claims the benefit of the filing date of U.S. Provisional Patent Application Ser. No. 63/184,318, filed May 5, 2021, entitled "SYSTEMS FOR TRANSCATHETER PROSTHESIS DELIVERY AND METHODS," the entire teachings of which are incorporated herein by reference.

FIELD

The present technology is generally related to systems, delivery devices, prostheses and methods for transcatheter delivery and deployment of a prosthesis, such as a prosthetic heart valve.

BACKGROUND

A human heart includes four heart valves that determine the pathway of blood flow through the heart: the mitral valve, the tricuspid valve, the aortic valve, and the pulmonary valve. The mitral and tricuspid valves are atrio-ventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of a prosthetic heart valve or prosthesis on the beating heart, intending to obviate the need for the use of classical sternotomy and cardiopulmonary bypass. In general terms, an expandable prosthetic valve is compressed about or within a catheter, inserted inside a body lumen of the patient, such as the femoral artery, and delivered to a desired location in the heart.

The heart valve prosthesis employed with catheter-based, or transcatheter, procedures generally includes an expandable multi-level frame or stent that supports a valve structure having a plurality of leaflets. The frame can be contracted during percutaneous transluminal delivery, and expanded upon deployment at or within the native valve. One type of valve stent can be initially provided in an expanded or uncrimped arrangement, then crimped or compressed about a balloon portion of a catheter. The balloon is subsequently inflated to expand and deploy the prosthetic heart valve. With other stented prosthetic heart valve designs, the stent frame is formed to be self-expanding. With these systems, the valved stent is crimped down to a desired size and held in that compressed state within a sheath for transluminal delivery. Retracting the sheath from this valved stent allows the stent to self-expand to a larger diameter, fixating at the native valve site. In more general terms, then, once the prosthetic valve is positioned at the treatment site, for instance within an incompetent native valve, the stent frame structure may be expanded to hold the prosthetic valve firmly in place.

The present disclosure addresses problems and limitations associated with the related art.

SUMMARY

The techniques of this disclosure generally relate to systems, delivery devices and methods for transcatheter delivery and deployment of a prosthesis, such as a prosthetic heart valve, to a defective heart valve. Aspects of the disclosure are particularly beneficial in that they can have a reduced delivery profile, provide improved device tracking, allow for a more controlled deployment of the prosthesis and can allow for a shorter prosthesis, which can improve maneuverability of the loaded device.

In one aspect, the present disclosure provides a prosthesis including a stent frame having an inner surface and an outer surface. The prosthesis can further include a valve structure positioned within the stent frame and a helical track formed by one or more guides positioned on and extending from the stent frame.

In another aspect, the disclosure provides a system including a delivery device having a handle assembly, a shaft assembly having a distal portion, and a helical elongated member positioned at least partially over the shaft assembly and interconnected to the handle assembly. The system also includes a prosthesis positioned over the distal portion. The prosthesis has a stent frame having an inner surface and an outer surface, a valve structure positioned within the stent frame, and a track formed by one or more guides positioned on and extending from the stent frame. The helical elongated member is configured to be moved in and out of the track.

In yet another aspect, the disclosure provides methods including providing a delivery device having a handle assembly, a shaft assembly having a distal portion, and a helical elongated member positioned at least partially over the shaft assembly and interconnected to the handle assembly. Methods include providing a prosthesis including a stent frame and a track formed by a plurality of guides, each guide defining an opening and extending from an inside surface of the stent frame. The method further includes actuating the handle assembly to rotate the helical elongated member to advance the helical elongated member distally through the track.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

As referred to herein, a stented prosthesis useful with the various systems, devices and methods of the present disclosure may assume a wide variety of configurations, such as a bioprosthetic heart valve having tissue leaflets or a synthetic heart valve having polymeric, metallic or tissue-engineered leaflets, and can be specifically configured for replacing valves of the human heart. Although the stented prosthesis of the present disclosure is described mainly as being self-expandable, the stented prosthesis can also be balloon expandable and/or mechanically expandable or combinations thereof. In general terms, the stented prosthesis of the present disclosure includes a stent or stent frame having an internal lumen maintaining a valve structure (tissue or synthetic), with the stent frame having a normal, expanded condition or arrangement and is collapsible to a compressed condition or arrangement for loading within the delivery device. For example, the stents or stent frames are support structures that comprise a number of struts or wire segments arranged relative to each other to provide a desired compressibility and strength to the prosthetic valve. The struts or wire segments are arranged such that they are capable of self-transitioning from, or being forced from, a compressed or collapsed condition to a normal, radially expanded condition. The struts or wire segments can be formed from a shape memory material, such as a nickel titanium alloy (e.g., Nitinol). The stent frame can be laser-cut from a single piece of material, or can be assembled from a number of discrete components.

Figure 1:
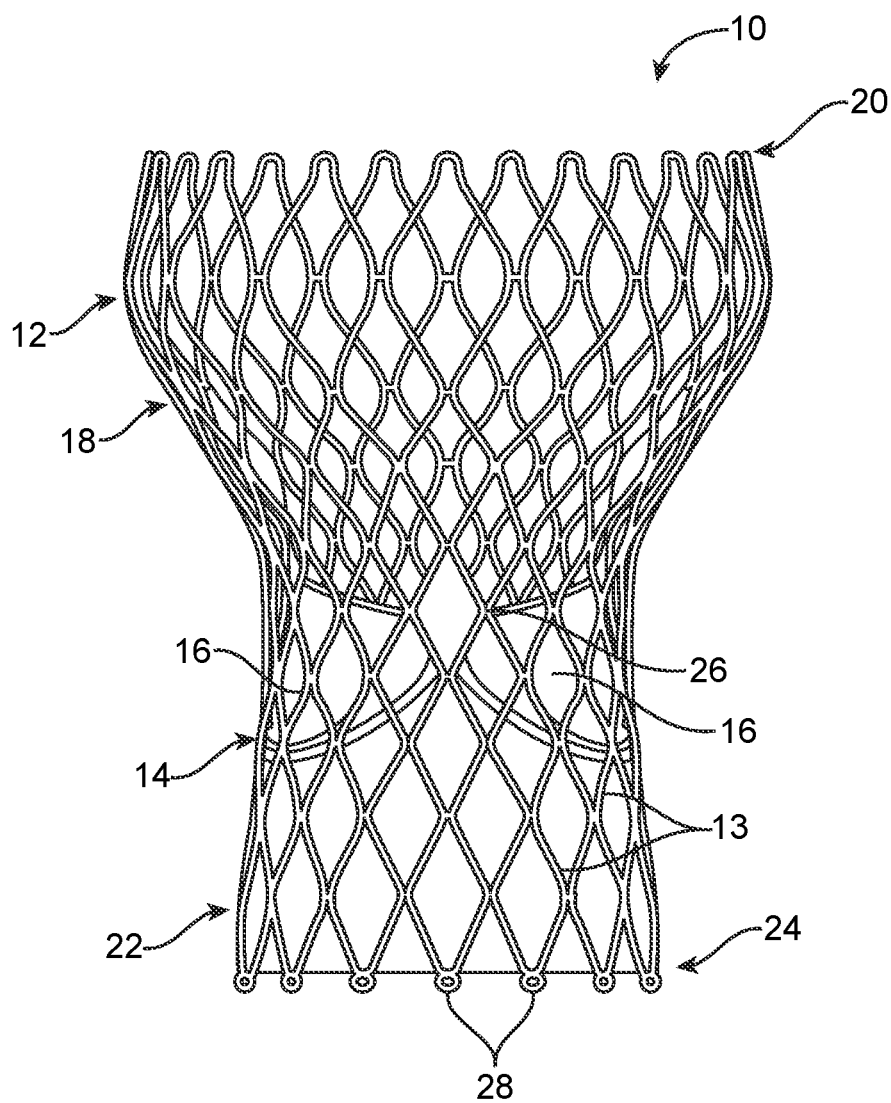
FIG. 1 is front view of a stented prosthetic heart valve that can be used with the delivery devices disclosed herein shown in an expanded arrangement.

One simplified, non-limiting example of a stented prosthesis 10 is illustrated in detail in FIG. 1. In this example, the stented prosthesis is a stented prosthetic heart valve. As a point of reference, the stented prosthesis 10 is shown in a normal or expanded state in the view of FIG. 1. The stented prosthesis 10 includes a stent or stent frame 12 formed at least in part by a plurality of struts 13 (generally referenced) and a valve structure 14. The stent frame 12 can assume any of the forms mentioned above. In some embodiments, the stent frame 12 is constructed to be self-expandable from the compressed state to the normal, expanded state. In some embodiments, the stent frame 12 is constructed to be balloon expandable from the compressed state to the normal, expanded state. In some embodiments, the stent frame 12 is constructed to be mechanically expandable from the compressed state to the normal, expanded state.

When present, the valve structure 14 of the stented prosthesis 10 can assume a variety of forms, and can be formed, for example, from one or more biocompatible synthetic materials, synthetic polymers, autograft tissue, homograft tissue, xenograft tissue, or one or more other suitable materials. In some embodiments, the valve structure 14 can be formed, for example, from bovine, porcine, equine, ovine and/or other suitable animal tissues. In some embodiments, the valve structure 14 can be formed, for example, from heart valve tissue, pericardium, and/or other suitable tissue. In some embodiments, the valve structure 14 can include or form one or more leaflets 16. For example, the valve structure 14 can be in the form of a tri-leaflet bovine pericardium valve, a bi-leaflet valve, or another suitable valve.

In some prosthetic valve constructions, such as that of FIG. 1, the valve structure 14 can comprise two or three leaflets that are fastened together at enlarged lateral end regions to form commissural joints, with the unattached edges forming coaptation edges of the valve structure 14. The leaflets 16 can be fastened to a skirt that in turn is attached to the stent frame 12. Alternatively, the leaflets 16 can be fastened directly to the stent frame 12. The stented prosthesis 10 includes an outflow portion 18 corresponding to a first or outflow end 20 (forcing out fluid) of the stented prosthesis 10. The opposite end of the stented prosthesis 10 can define an inflow portion 22 corresponding to a second or inflow end 24 (receiving fluid). As shown, the stent frame 12 can have a lattice or cell-like structure, and optionally forms or provides posts 26 corresponding with commissures of the valve structure 14 as well as eyelets 28 (or other shapes) at either or both of the outflow and inflow ends 20, 24. If provided, the posts 26 are spaced equally around stent frame 12 (only one post 26 is clearly visible in FIG. 1). It will be understood that aspects of the disclosure can also be applied and used to reconfigure and deliver other stented implants as well in similar manners.

Referring now in addition to FIGS. 2A-4, which schematically illustrate a system 100 of the disclosure. Generally, the system 100 includes a prosthesis 110 and a delivery device 160. The prosthesis 110 can be configured similarly to that of FIG. 1 except as explicitly stated. The delivery device 160 is arranged and configured for percutaneously delivering the stented prosthesis 110 or other stented prosthesis (hereinafter "prosthetic valve" or "prosthesis") to a patient's native defective heart valve, for example. In one example, the delivery device 160 can include an outer sheath assembly 162, a shaft assembly 164 and a handle assembly 180. The delivery device 160 provides a loaded, compressed arrangement (FIG. 2B) in which the prosthesis 110 is loaded over the shaft assembly 164 and is compressively retained on a distal portion 167 of the shaft assembly 164 by the outer sheath assembly 162. Particularly, the outer sheath assembly 162 includes a helical elongated member 170 at a distal end 163 of the outer sheath assembly 162. The helical elongated member 170 is configured to engage a track 130 of the prosthesis 110 to selectively compress the prosthesis 110.

Figure 2A:
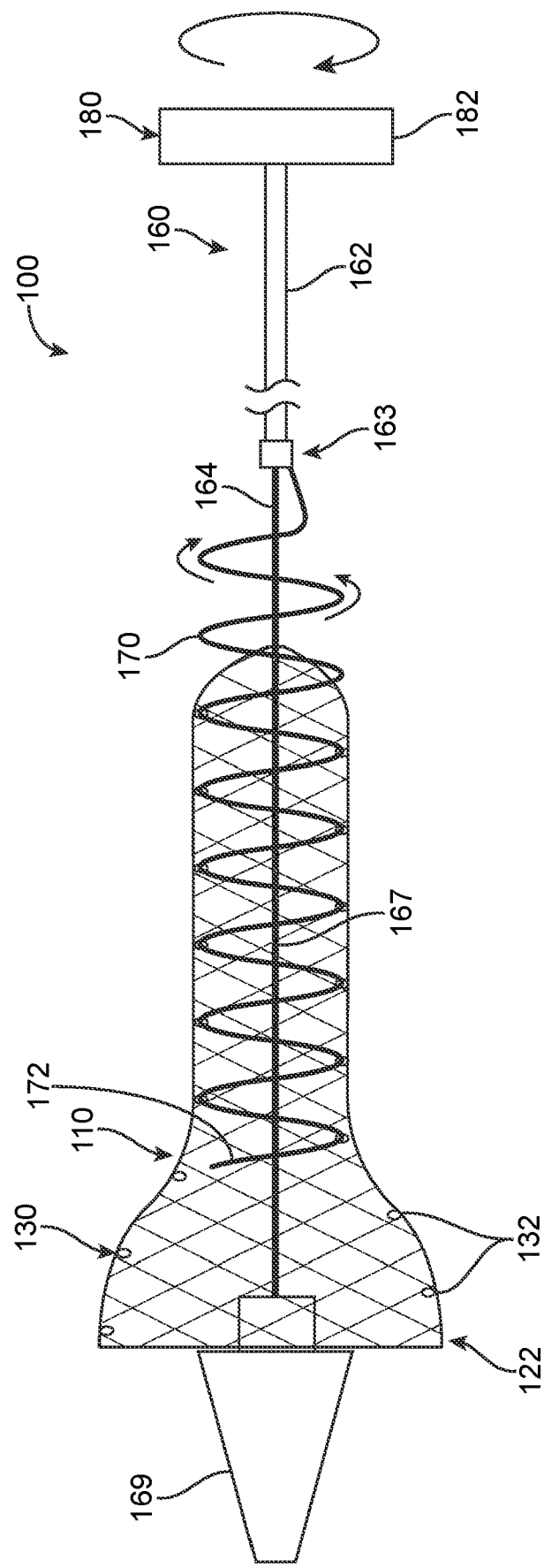
FIG. 2A is a perspective view of a delivery device for delivering a stented prosthetic heart valve or other stented prosthesis in a loaded arrangement.
Figure 2B:
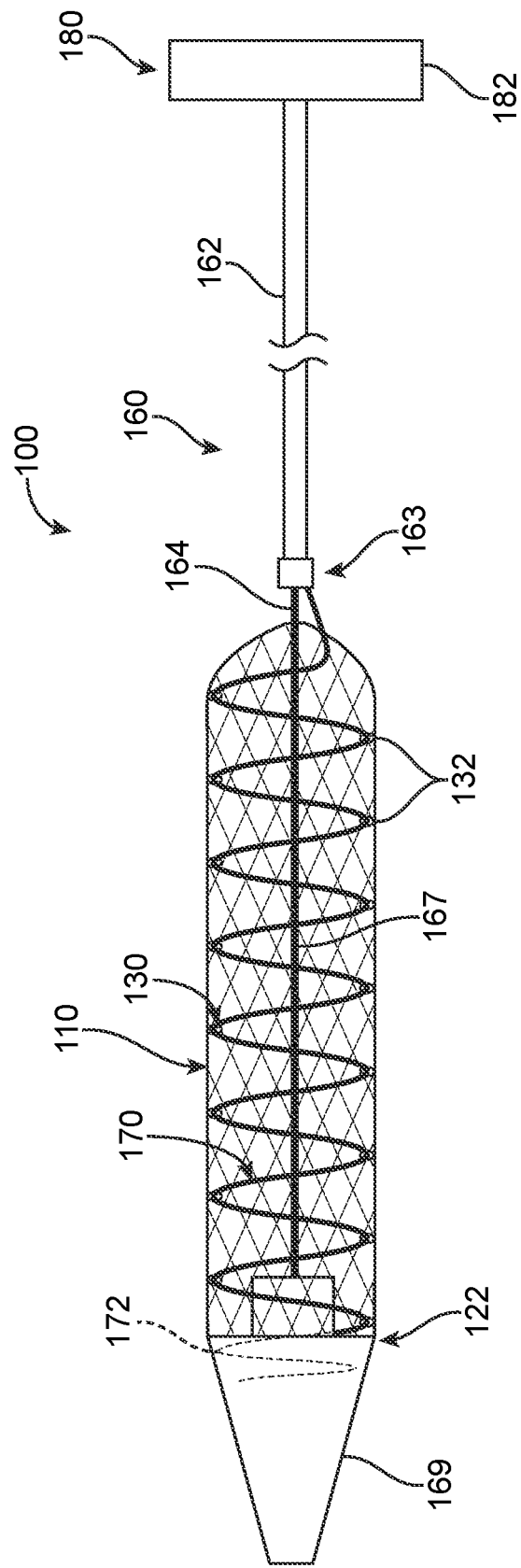
FIG. 2B is a partial, schematic illustration of the delivery device of FIG. 2A in a partially, deployed or partially loaded arrangement.

As the helical elongated member 170 advances within the track 130, the helical elongated member 170 compresses at least a portion of the prosthesis 110 to reduce the system 100 profile for transcatheter delivery (see the transition between FIGS. 2A and 2B). In one example, the distal portion 167 terminates at a nose cap 169 and the distal end 172 of the helical elongated member 170 is tucked into the nose cap 169 in the loaded arrangement as is shown in FIG. 2B. Once loaded and compressed in the arrangement of FIG. 2B, the prosthesis 110 is located at a target site and then the helical elongated member 170 can be proximally withdrawn from the track 130 to allow the prosthesis 110 to at least partially self-expand (FIG. 2A). The helical elongated member 170 can be further proximally withdrawn to ultimately fully deploy the prosthesis 110 from the delivery device 160.

In various examples of the disclosure, the helical elongated member 170 spans at least 90% of a length L of the prosthesis 110 in the loaded arrangement. In another example, the helical elongated member 170 spans 100% of the length L of the prosthesis 110 in the loaded arrangement. In embodiments where the helical elongated member 170 does not span the entire length of the prosthesis 110, a distal portion 122 of the prosthesis 110 can be optionally compressed in another manner, such as with a suture or the like, which can be severed prior to deployment of the prosthesis 110.

Figure 3A:
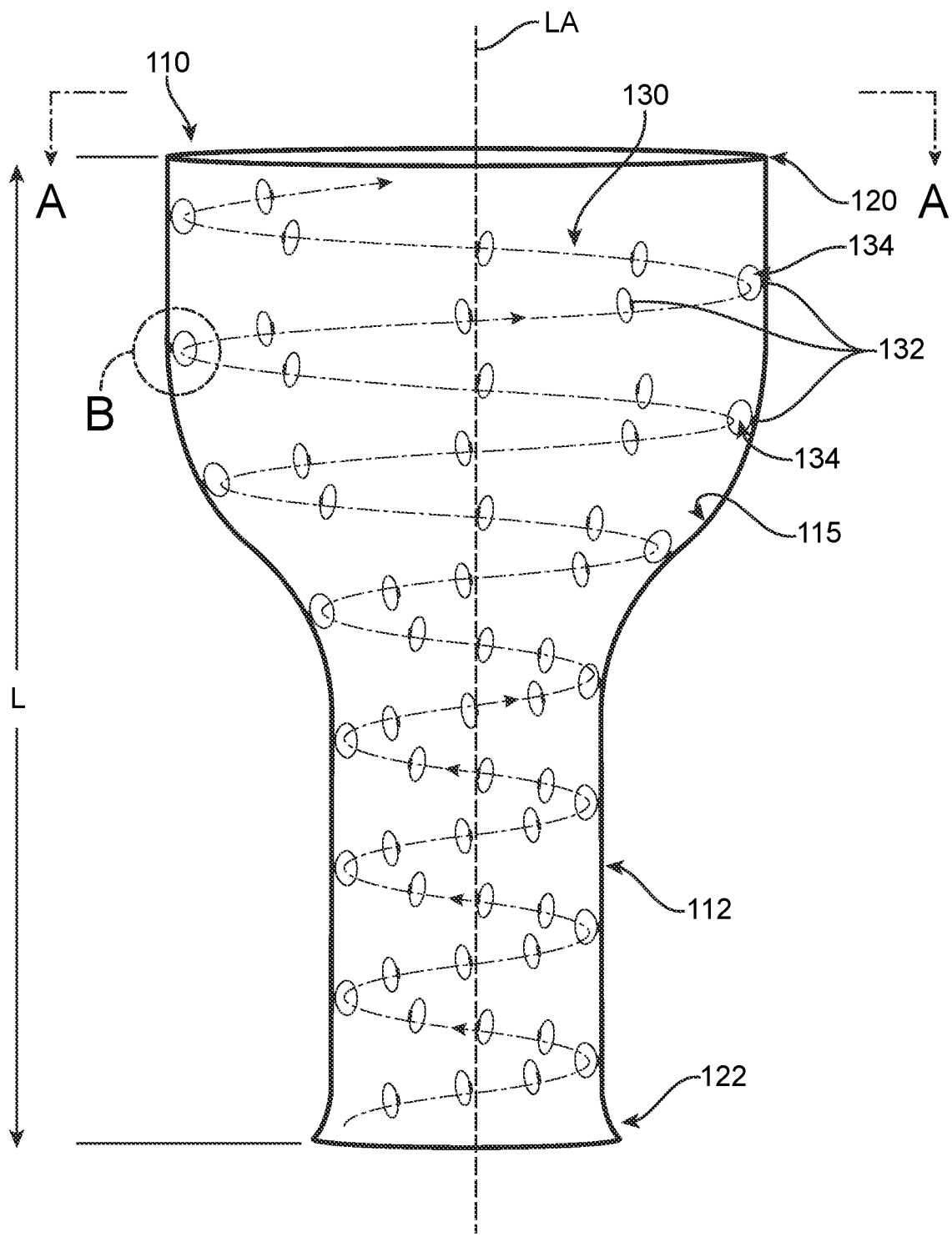
FIG. 3A is a schematic side view of an alternate stented prosthetic heart valve of the disclosure in an expanded arrangement, the stented prosthetic heart valve having a track including a plurality of guides.
Figure 3B:
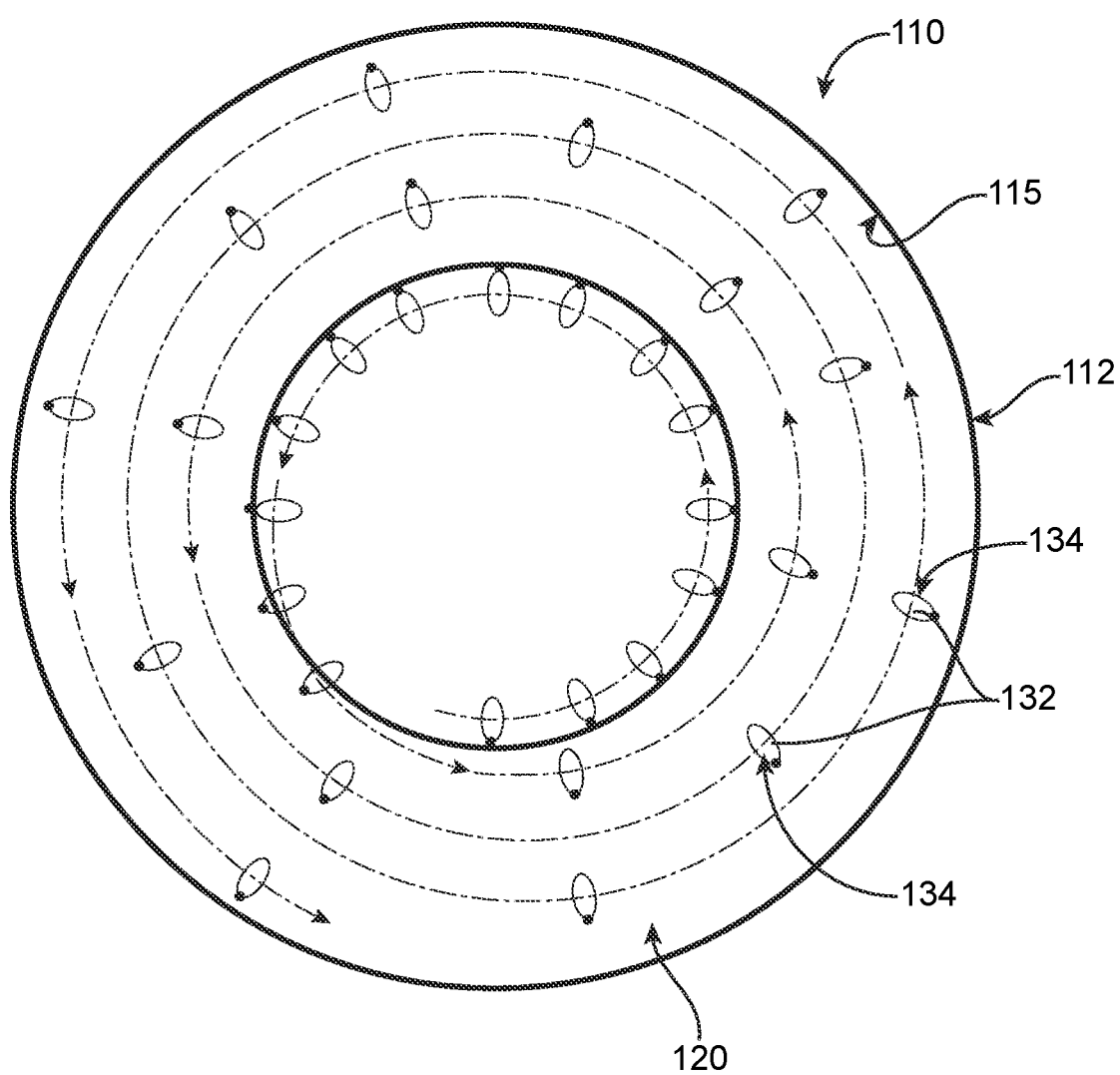
FIG. 3B is a top view of the stented prosthetic heart valve of FIG. 4A as viewed from A-A.
Figure 4:
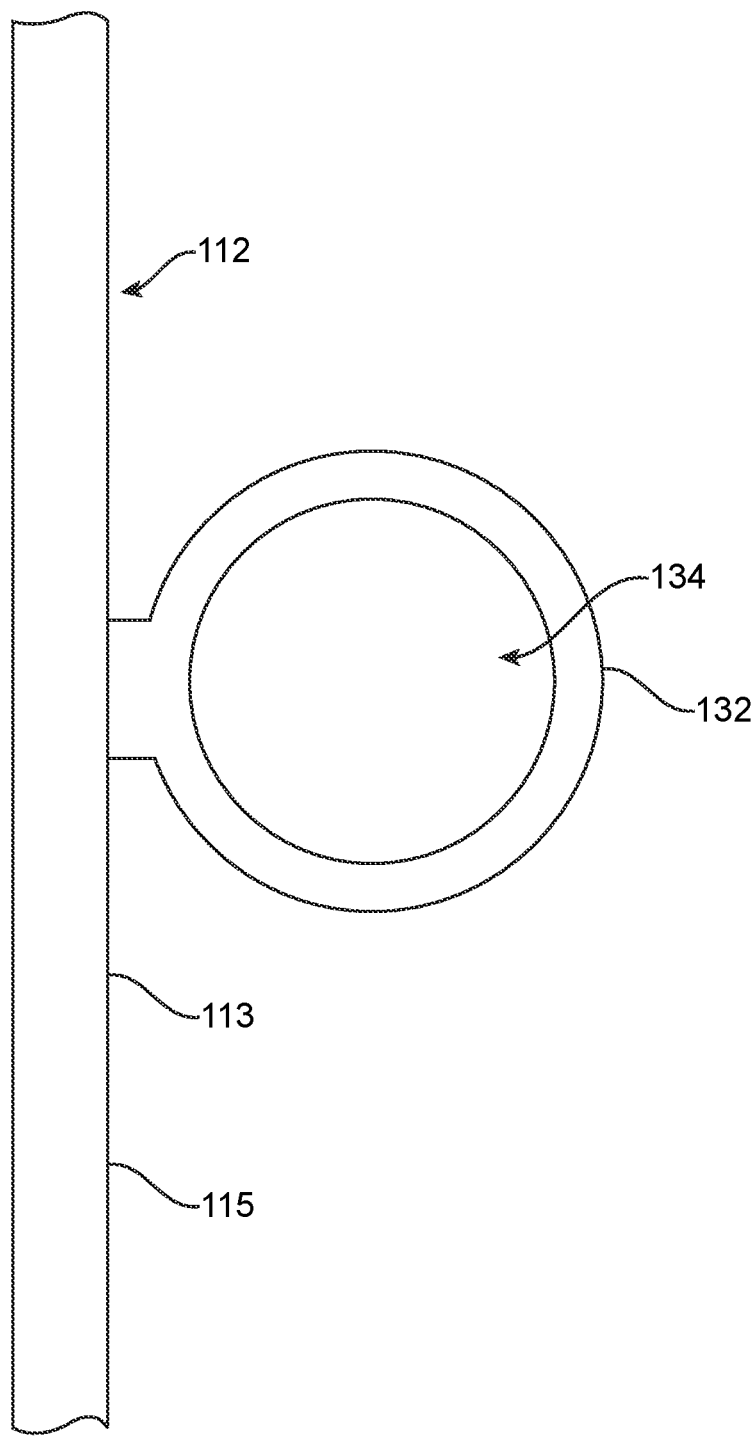
FIG. 4 is a partial, enlarged view of Sec. B of FIG. 3B showing one guide of the track of the stented prosthetic heart valve of FIGS. 4A-4B.
Figure 5A:
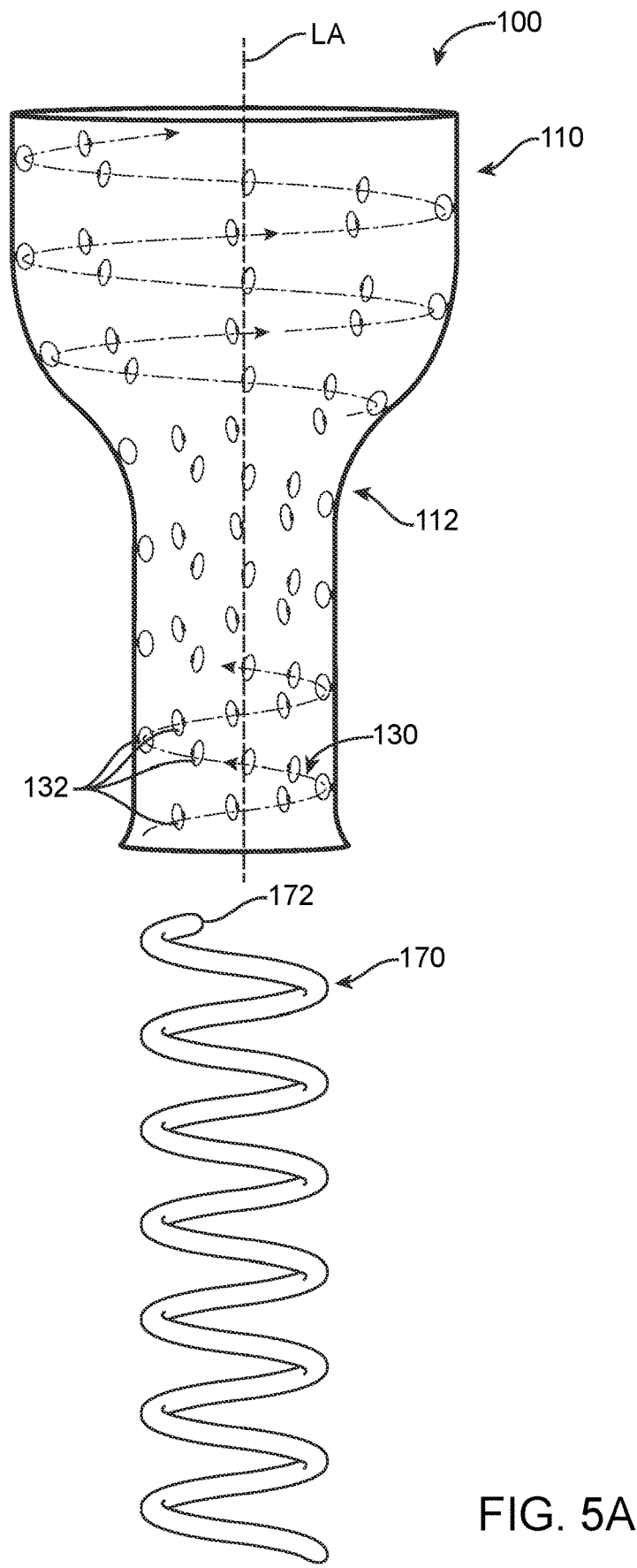
FIG. 5A is a partial, side view of an alternate system of the disclosure including a delivery device having a stented prosthetic heart valve loaded thereto.
Figure 5B:
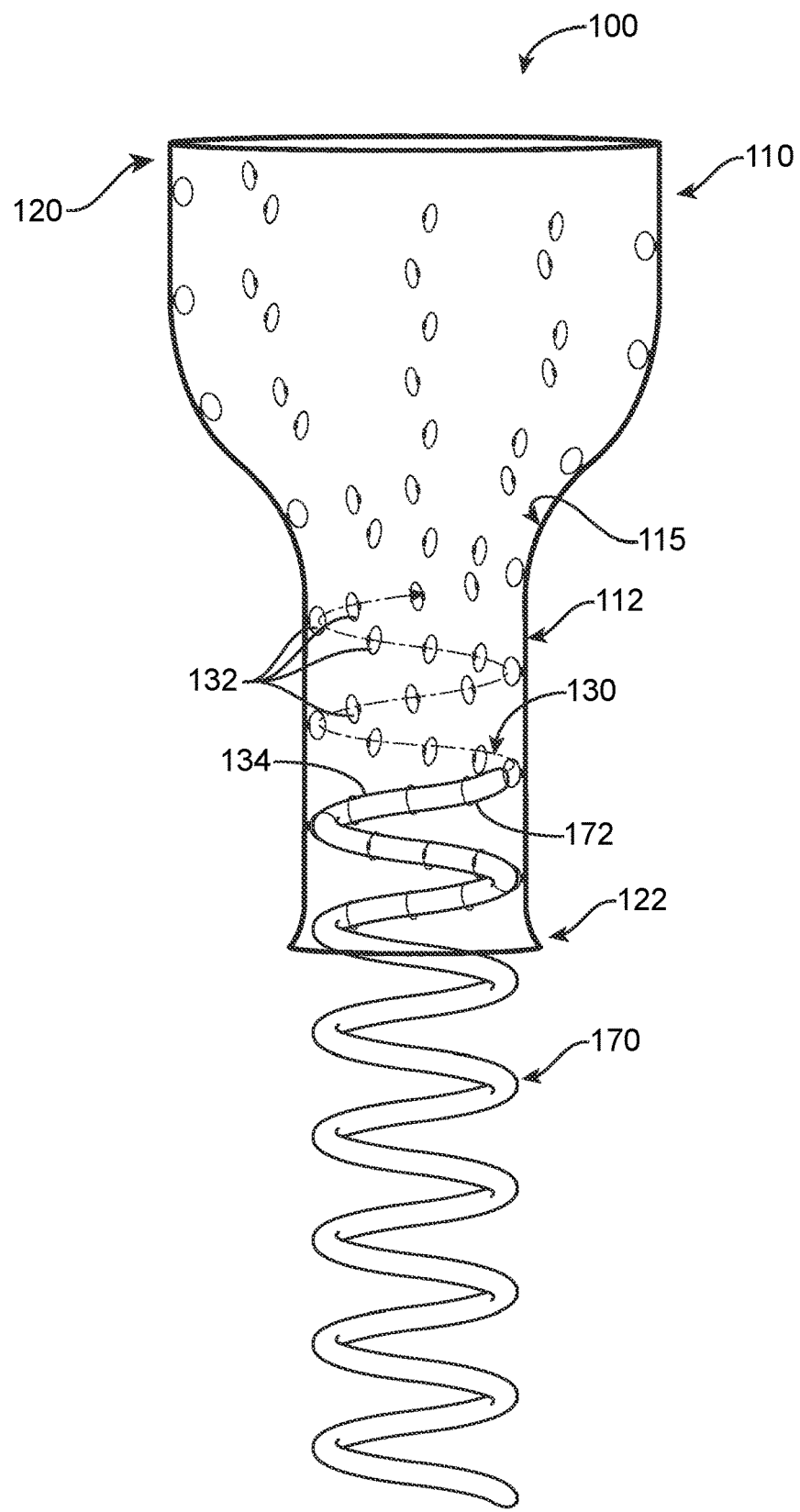
FIGS. 5B-5C are side views of the system of FIG. 5A with the stented prosthetic heart valve being partially-loaded or partially-deployed.
Figure 5C:
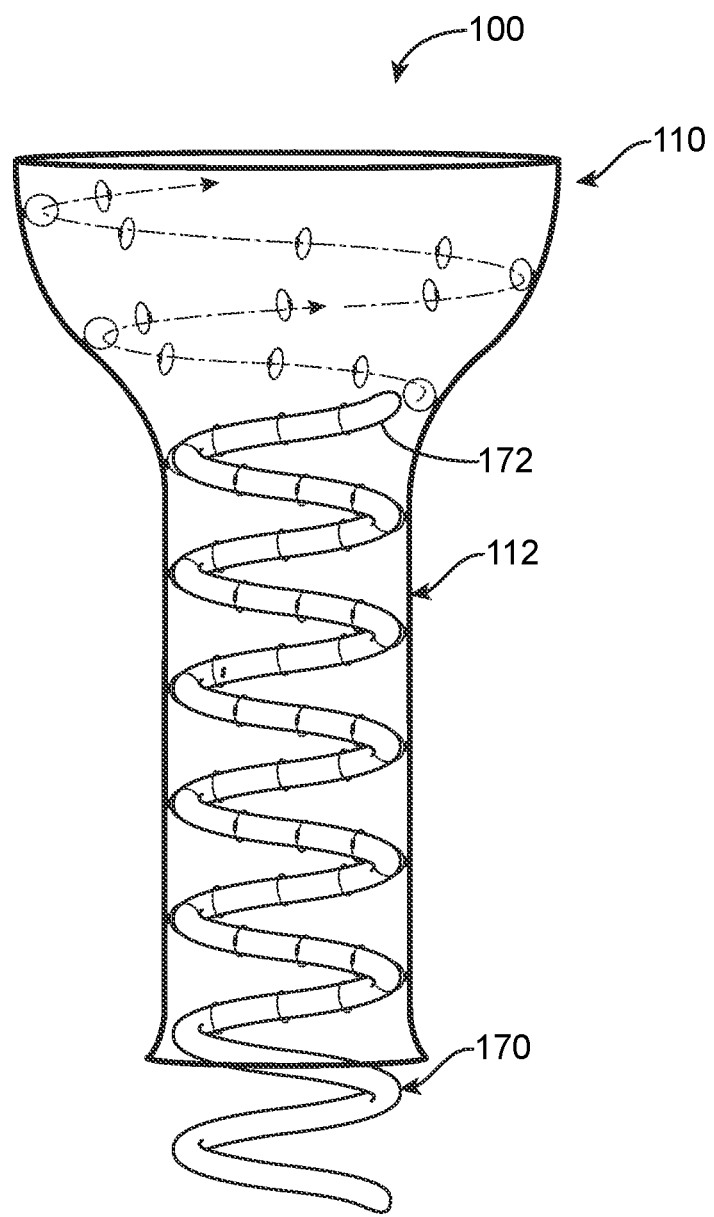
Figure 5D:
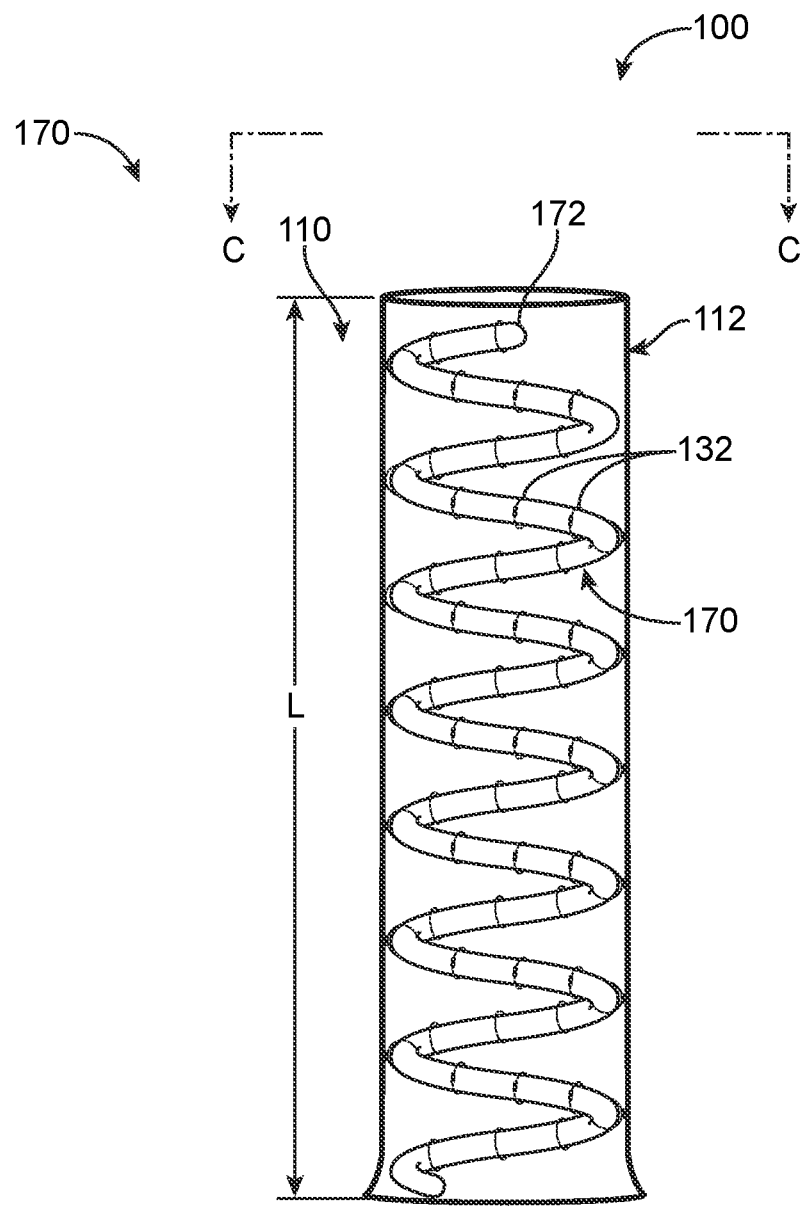
FIG. 5D is a side view of the system of FIGS. 5A-5C in a loaded arrangement.
Figure 5E:
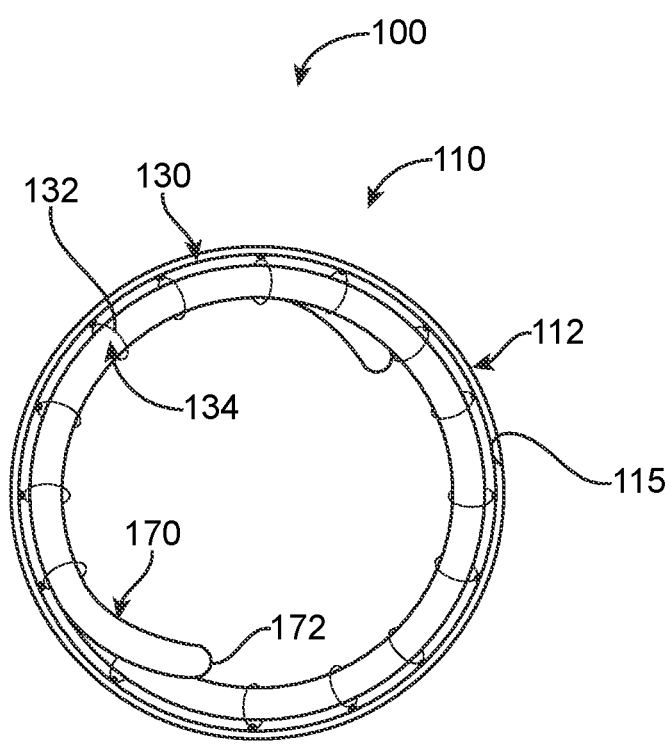
FIG. 5E is a top view of the system of FIGS. 5A-5D in the loaded arrangement of FIG. 5D as viewed from C-C.

Referring now specifically to FIGS. 3A-4, which schematically illustrate the prosthesis 110 in greater detail. In this example, the prosthesis 110 includes a stent frame 112 formed by a plurality of struts 113 similar to that of FIG. 1, however the frame 112 and struts 113 are shown schematically for ease of illustration (see, in particular, FIG. 4). The prosthesis 110 may include a valve structure (not shown for ease of illustration; e.g., valve structure 14 of FIG. 1) and can otherwise be identically configured to any prosthesis disclosed herein except as explicitly stated. As indicated above, the prosthesis 110 includes the track 130 that extends radially inwardly from the stent frame 112. In other words, the track 130 is positioned within the stent frame 112, extending radially in a direction toward a central longitudinal axis LA of the stent frame 112. In the example shown, the track 130 is formed by a plurality of guides 132 collectively arranged in a helical fashion around an inside or inner surface 115 (generally referenced) of the stent frame 112. Therefore, it can also be said that the track 130 has a helical configuration. Each guide 132 can take a variety of forms. In the example of FIGS. 2A-5B, each guide 132 can define an enclosed opening 134 (only a select few are referenced for ease of illustration). It is further envisioned that the guides 132 can be similarly configured or can have varying configurations.

As perhaps best shown in FIGS. 5A-5E, the guides 132 forming the track 130 are cooperatively configured to receive the helical elongated member 170. When the helical elongated member 170 is advanced through the respective openings 134 in the guides 132, the prosthesis 110 is pulled from an expanded arrangement (FIGS. 5A-5B) to a partially-compressed arrangement (FIG. 5C) and then into a compressed arrangement (FIG. 5D-5E) for delivery or recapture of the prosthesis 110. In such an example, the helical elongated member 170 is rotating advanced or withdrawn about the longitudinal axis LA of the prosthesis 110 and the distal portion 167 over which the prosthesis 110 is positioned. Actuation or movement of the helical elongated member 170 can optionally be controlled by a handle assembly 180 of the delivery device 160, for example. The helical elongated member 170 can be connected to or integrally formed with the catheter or sheath assembly 162. In one example, the handle assembly 180 can include an actuator 182 that can be rotated clockwise to move the helical elongated member in one direction and the actuator 182 can be rotated counter-clockwise to rotate and advance the helical elongated member 170 in a second, opposing direction.

In various embodiments, one or more guides of any tracks of the disclosure are made of a bioresorbable material such as a bioresorbable polymer or bioresorbable metal (e.g., magnesium or iron based alloys such as magnesium poly-l-lactic acid (PLLA)) or the like. In other various embodiments, the guides are made of a surgical metal (e.g., nitinol) that can be riveted or otherwise connected to the stent frame, for example.

Figure 6:
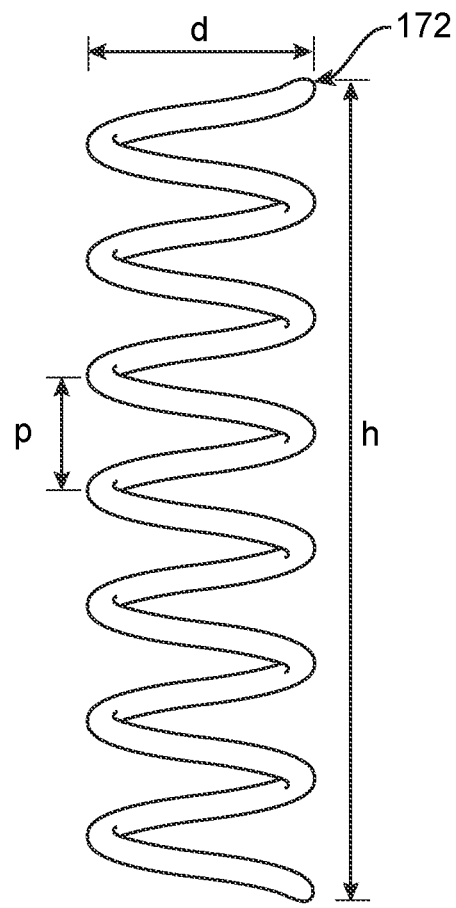
FIG. 6 is a side view of a helical elongated member of the disclosure.

Referring in addition to FIG. 6, in one example, the helical elongated member 170 has the following parameters considering the crimped length and diameter of a transcatheter valve prosthesis (e.g., prosthesis 110):

Height, h=40 mm
Pitch, p=5 mm
Diameter, d=10 mm
Circumference, C=πd
   C=π(10)
   C=31.42 mm
Number of turns, $$n = \frac{h}{p}$$

$$n = \frac{40}{5}$$

$n = 8$ turns

Overall length of helix wire material $$L = n\sqrt{c^2 + p^2} = 8\sqrt{(31.42)^2 + 5^2} = 254.52 \text{ mm}$$

Based on the above, 254.52 mm of wire material length is required to make a helical elongated member with a height of 40 mm, pitch of 5 mm and diameter of 10 mm. Other examples can be obtained and determined using the aforementioned calculations.

The helical elongated members (e.g., helical elongated member 170) of the disclosure can take many configurations. Generally, the helical elongated member can include a helical wire having diameter in the range of 1.5 mm to 2 mm. In one non-limiting example, the helical wire is made of stainless steel. In other examples, the pitch p of the wire is configured to hold the prosthesis 110 in a compressed configuration until the prosthesis is deployed. In one example, a minimum pitch p or gap between wraps or turns comprising the helical elongated member is at least 3 mm.

In one method of the disclosure, the prosthesis 110 is positioned over the distal portion of the delivery device 160 (FIG. 2A). From a location proximal to the prosthesis 110, the actuator of the handle assembly is rotated or otherwise actuated to distally advance the helical elongated member 170 from a position proximal to the track 130 to a position with the helical elongated member 170 within the track 130 (i.e. within one or more guides 132) located on the inside surface of the stent frame 112 of the prosthesis 110. As the helical elongated member 170 is distally advanced, the helical elongated member 170 rotates about the distal portion and longitudinal axis LA, one guide 132 at a time until the helical elongated member 170 spans at least 90% of a length L of the prosthesis 110. With the helical elongated member 170 being in the compressed arrangement yet unsheathed or otherwise uncovered as shown in FIG. 2B, the prosthesis 110 is then delivered with the delivery device 160 via a transcatheter procedure to a target site, such as at a native heart valve. In one example, the native heart valve is a mitral heart valve. Proper positioning of the prosthesis 110 in the atrium, proximal to the annulus can be confirmed via imaging techniques. Once the physician navigates the prosthesis 110 to the desired position, the prosthesis can be transitioned to a partially expanded arrangement with the actuator to rotationally move the helical elongated member 170 in a proximal direction and correspondingly free the prosthesis 110 from the forces of the helical elongated member 170 so that the distal end of the prosthesis 110 is allowed to naturally expand. Should recapture of the prosthesis be desired, the actuator can be rotated in the opposite direction to distally advance the helical elongated member 170 in the same manner to compress the prosthesis 110. When the helical elongated member 170 is fully withdrawn and disengaged from the track 130 at a position proximal to the prosthesis 110, the prosthesis is then fully seated in the patient's anatomy. The delivery device 160 can be withdrawn from the patient in the same manner as it was delivered.

Figure 7A:
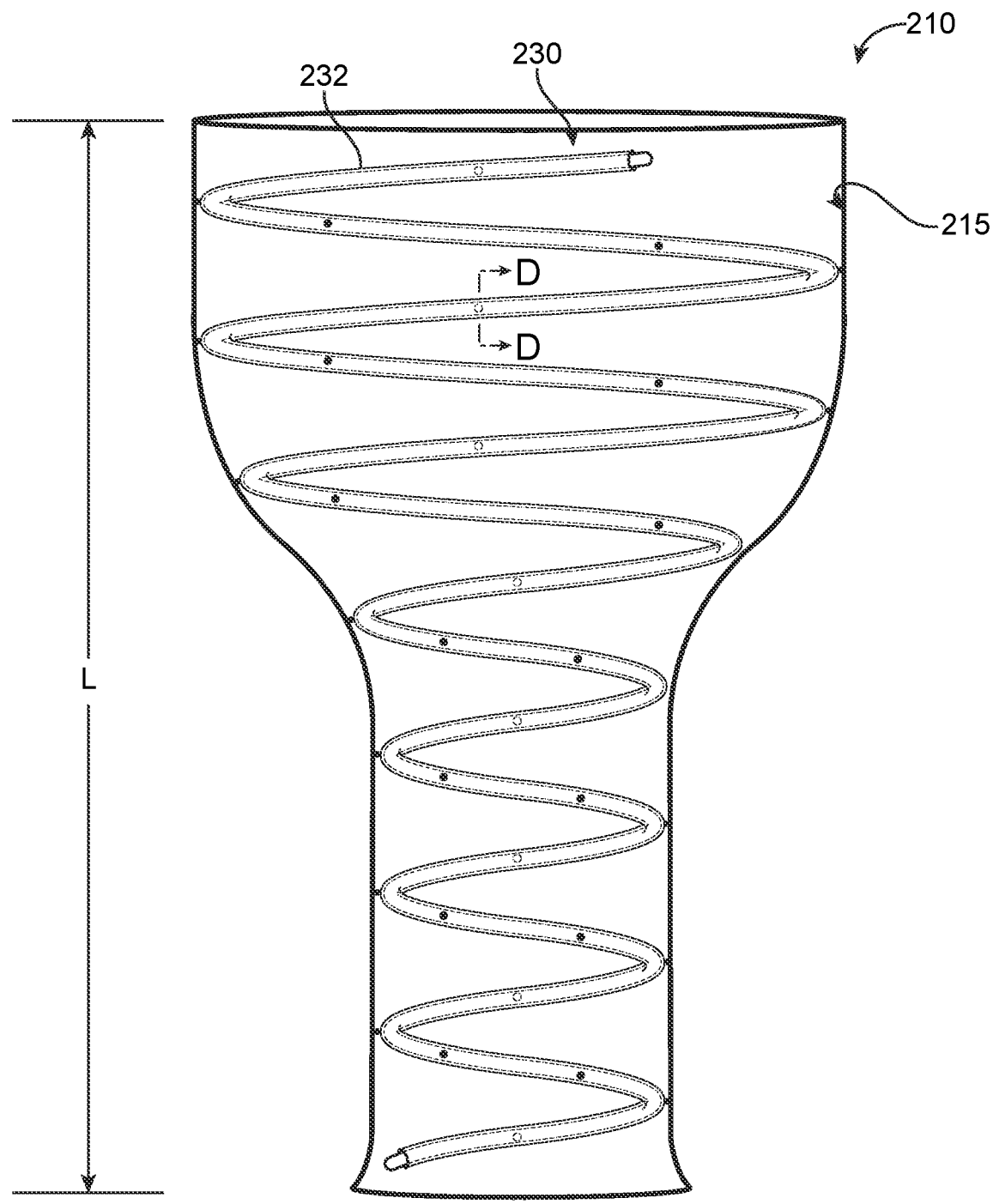
FIG. 7A is a schematic side view of an alternate stented prosthetic heart valve of the disclosure in an expanded arrangement, the stented prosthetic heart valve having a track including a single, enclosed guide.
Figure 7B:
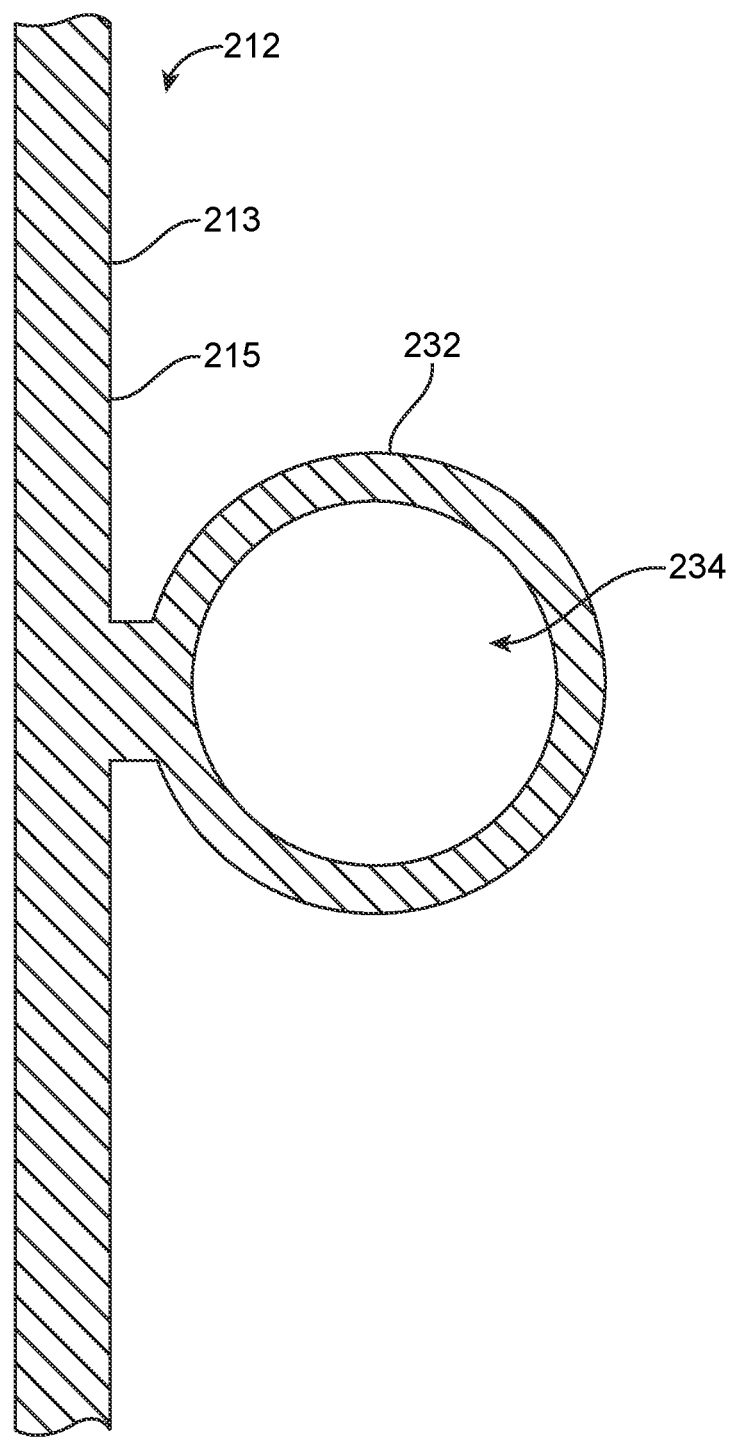
FIG. 7B is a partial, cross-sectional view of the track of FIG. 7A as viewed along line D-D.

Referring in addition to FIGS. 7A-7B, which schematically illustrate an alternate prosthesis 210, which can be identically configured and used as compared to prosthesis 10 or 110 except as explicitly stated. In this example, the prosthesis 210 includes a track 230 extending radially inward from an inside surface 215 of a stent frame 212 having a plurality of struts 213 similar to that shown in FIG. 1, for example. In this example, the track 230 includes a single helical guide 232 defining an opening 234, which is configured to receive the helical elongated member 170. The guide 232 extends from the inside surface 215 of the stent frame 212 in a direction of a longitudinal axis of the stent frame 212. In various examples, the track 230 spans at least 90% of a length L of the prosthesis 210. In some examples, the track 230 spans 100% of the length L of the prosthesis 210. In alternate embodiments, the guide 232 can be split into multiple helical guides defining respective helical openings, each guide forming a portion of the track. Similar to FIG. 2B, when the helical elongated member 170 of the delivery device 160 is fully inserted within the track 230, the prosthesis 210 is compressed for delivery in a loaded arrangement.

Figure 8:
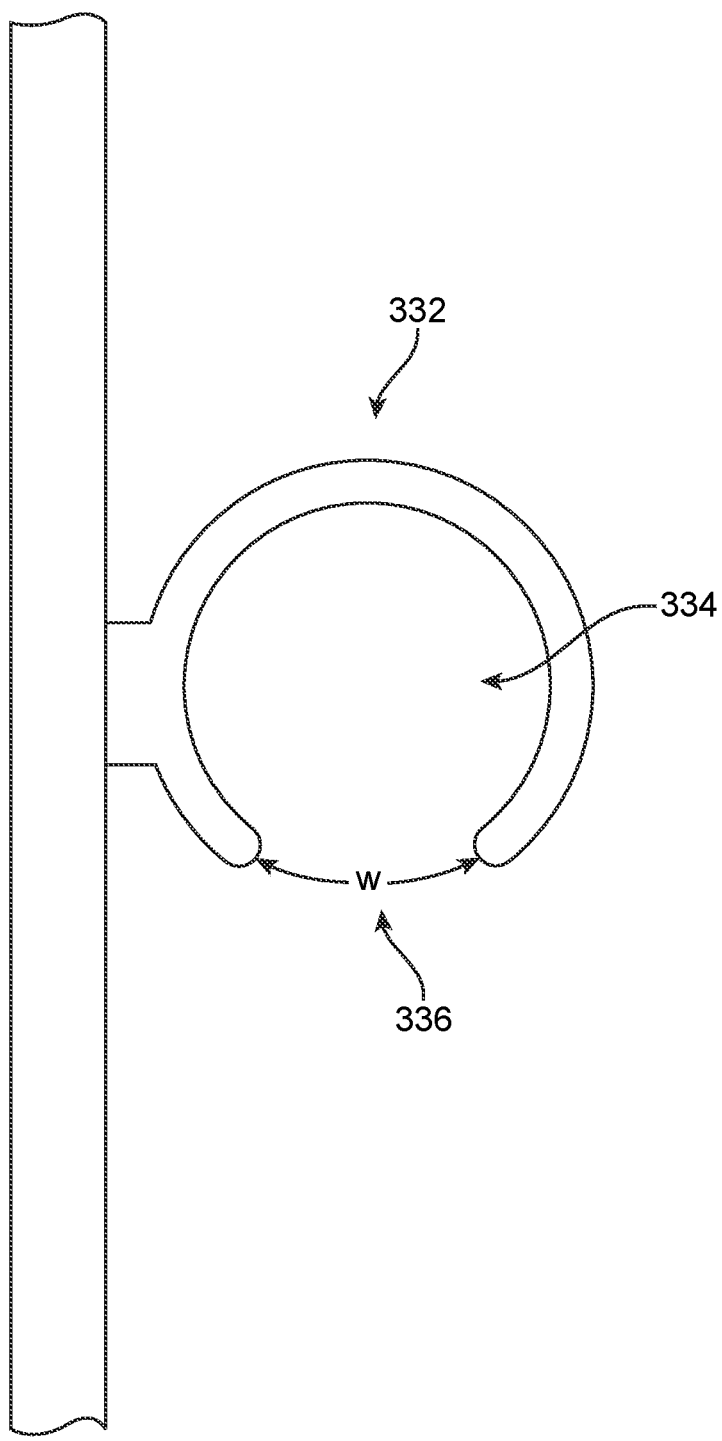
FIG. 8 is a partial, cross-sectional view of an alternate guide.

Referring now in addition to FIG. 8, any guide disclosed herein can include an opening that is partially-enclosed. For example, the guide 332 includes an opening 334 that is partially enclosed. The guide 332 is configured to retain the helical elongated member 170. Therefore, a cutout 336 in the guide 332 may be configured to have a width "w" that is less than a diameter of the wire forming the helical elongated member 170.

Figure 9A:
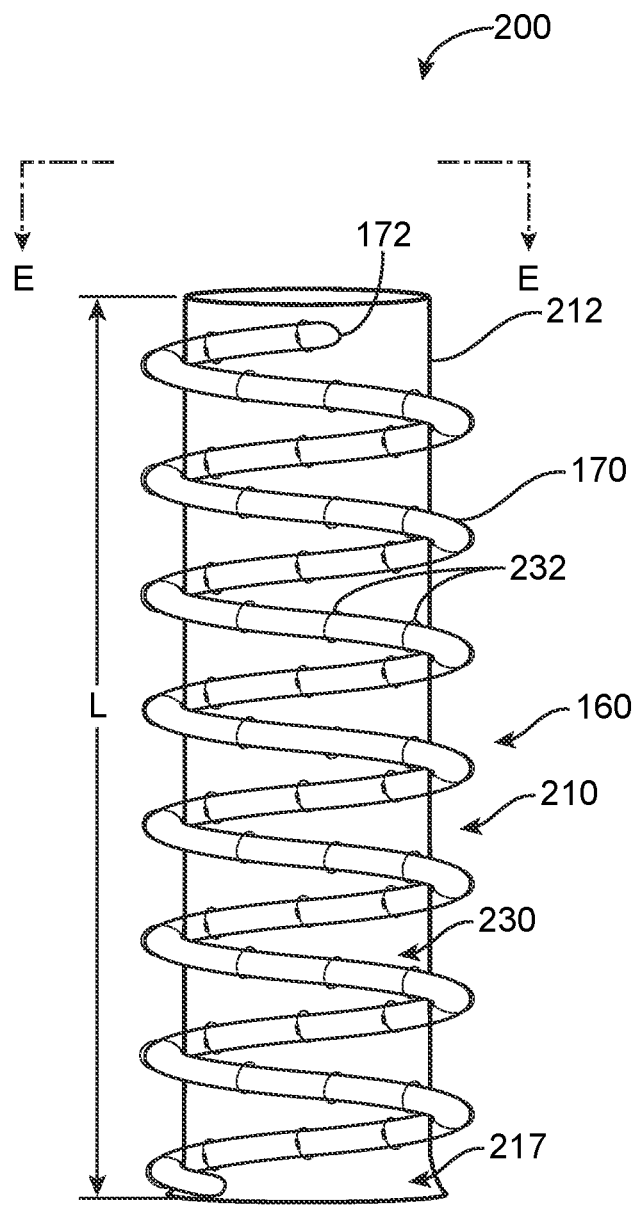
FIG. 9A is a partial, side view of an alternate system in a loaded arrangement.
Figure 9B:
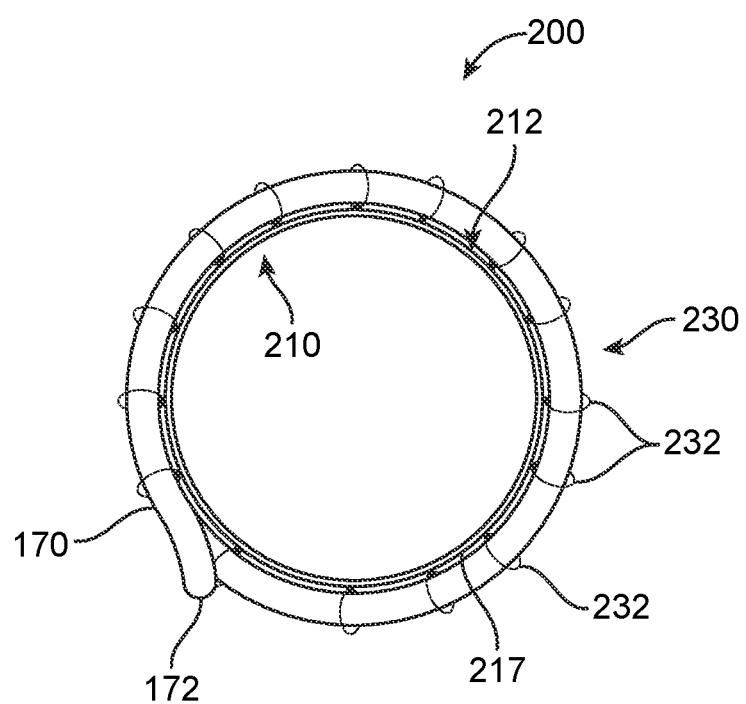
FIG. 9B is a top view of the system of FIG. 9A as viewed along line E-E.

Referring now in addition to FIGS. 9A-9B, which schematically illustrate an alternate system 200 of the disclosure. Generally, the system 200 is identical in configuration and use as compared to system 100 except as explicitly stated. System 200 includes a prosthesis 210 and the delivery device 160. The prosthesis 210 can be configured similarly to prosthesis 10 or 110 with the exception that the prosthesis 210 includes a track 230 for helical elongated member 170 position on and extending outwardly from an outer surface 217 of the stent frame 212 (as compared to the track 130 being positioned on the inner surface 115 of the stent frame 112). In the example shown, the track 230 includes a plurality of guides 232 (generally referenced) that each extend radially outward from the outer surface 217. The track 230 can include one or more guides having any alternate configuration disclosed herein with respect to other embodiments.

Similar to prior embodiments, as the helical elongated member 170 advances within the track 230, the helical elongated member 170 compresses at least a portion of the prosthesis 210 to reduce the system 200 profile for transcatheter delivery (FIGS. 9A-9B). Once loaded and compressed in the arrangement of FIGS. 9A-9B, the prosthesis 210 is located at a target site and then the helical elongated member 170 can be proximally withdrawn from the track 230 to allow the prosthesis 210 to at least partially self-expand. The helical elongated member 170 can be further proximally withdrawn to ultimately fully deploy the prosthesis 210 from the delivery device 160 similar to the delivery and deployment of prosthesis 110 disclosed herein.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A prosthesis comprising:
   a stent frame having an inner surface and an outer surface;
   a valve structure positioned within the stent frame; and
   a helical track formed by one or more guides extending inwardly from the inner surface of the stent frame, wherein at least one of the one or more guides defines an enclosed opening.

2. The prosthesis of claim 1, wherein the track is formed by a plurality guides.

3. The prosthesis of claim 1, wherein at least one of the one or more guides is bioresorbable.

4. A system comprising:
   a delivery device including:
      a handle assembly comprising an actuator, a shaft assembly including a distal portion, and a helical elongated member positioned at least partially over the shaft assembly and interconnected to the handle assembly; and a prosthesis positioned over the distal portion, the prosthesis including:

a stent frame, a valve structure positioned within the stent frame, and a track formed by one or more guides extending from the stent frame, wherein the actuator of the handle assembly is configured to rotate the helical elongated member about a longitudinal axis of the prosthesis such that a distal end of the helical elongated member is received within the track to advance the helical elongated member distally through the track.

5. The system of claim 4, wherein the track spans at least 90% of a length of the prosthesis.

6. The system of claim 5, wherein, in a loaded arrangement, the helical elongated member spans 100% of a length of the prosthesis.

7. The system of claim 4, wherein the track is helical.

8. The system of claim 4, wherein an opening of the one or more guides defines an enclosed opening.

9. The system of claim 4, wherein an opening of the one or more guides is partially enclosed.

10. The system of claim 4, wherein one of the one or more guides is bioresorbable.

11. The system of claim 4, wherein the one or more guides includes one guide defining a helical channel.

12. The system of claim 4, wherein the helical elongated member is configured to compress the stent frame when positioned within the track.

13. A method comprising:

providing a delivery device including:

a handle assembly, a shaft assembly having a distal portion, and a helical elongated member positioned at least partially over the shaft assembly and interconnected to the handle assembly;

providing a prosthesis including a stent frame and a track formed by a plurality of guides spaced apart from one another in series along a path, each guide of the plurality of guides defining an opening and extending from the stent frame; and actuating the handle assembly to rotate the helical elongated member, wherein a distal end of the helical elongated member is successively received by each guide of the series along the path to advance the helical elongated member distally through the track, wherein portions of the prosthesis are radially compressed over the distal portion of the shaft assembly as the helical elongated member is distally advanced along the portions of the prosthesis.

14. The method of claim 13, wherein the step of distally advancing the helical elongated member within the track compresses the stent frame.

15. The method of claim 13, further comprising the step of delivering the prosthesis to a heart valve and proximally withdrawing the helical elongated member to at least partially allow the prosthesis to expand.

16. The method of claim 15, further comprising the step of distally advancing the helical elongated member along the portions of the prosthesis to recompress the prosthesis.

17. The method of claim 13, wherein the track includes at least one guide that is bioresorbable.

18. The method of claim 13, wherein the step of advancing the helical elongated member includes advancing the helical elongated member distally through the track until the helical elongated member spans at least 90% of a length of the stent frame.

19. The method of claim 13, wherein the track is helical.

20. The method of claim 13, wherein each guide of the plurality of guides extends inwardly from an inner surface of the stent frame.

* * * * *